(12) United States Patent
Birkel et al.

(10) Patent No.: US 7,597,898 B2
(45) Date of Patent: *Oct. 6, 2009

(54) AEROSOL FOAM OR PUMP FOAM PRODUCT FOR HAIR TREATMENT

(75) Inventors: Susanne Birkel, Darmstadt (DE); Harald Wendel, Ober-Ramstadt (DE); Michael Franzke, Rossdorf (DE); Manuela Hannich, Egelsbach (DE)

(73) Assignee: Wella AG, Darmstadt (DE)

(*) Notice: Subject to any disclaimer, the term of this patent is extended or adjusted under 35 U.S.C. 154(b) by 233 days.

This patent is subject to a terminal disclaimer.

(21) Appl. No.: 10/435,953

(22) Filed: May 12, 2003

(65) Prior Publication Data

US 2004/0228809 A1      Nov. 18, 2004

(30) Foreign Application Priority Data

May 5, 2002   (DE) ............................. 102 21 449

(51) Int. Cl.
*A61K 8/02* (2006.01)
*A61K 8/00* (2006.01)

(52) U.S. Cl. .................. 424/401; 424/407; 424/43; 424/45

(58) Field of Classification Search ................. 424/70.1
See application file for complete search history.

(56) References Cited

U.S. PATENT DOCUMENTS

| | | | |
|---|---|---|---|
| 3,472,840 A | 10/1969 | Stone et al. | |
| 5,690,924 A | 11/1997 | Keil et al. | |
| 6,149,898 A | 11/2000 | Peffly et al. | |
| 6,248,313 B1 | 6/2001 | Wachter et al. | |
| 6,264,929 B1 | 7/2001 | Karlen et al. | |
| 6,383,477 B1 | 5/2002 | Lede et al. | |

FOREIGN PATENT DOCUMENTS

| | | |
|---|---|---|
| WO | 96/00565 | 1/1996 |
| WO | 99/66888 | 12/1999 |

OTHER PUBLICATIONS

National Starch specification for polyquaternium-4, CELQUAT L-200 and CELQUAT H-100.*
E. Sagarin; "Cosmetics, Science and Technology", Interscience Publishers Inc, NY 1957, pp. 503-530 (in English).
H. Janistyn: "Handbook of Cosmetics and Fragrances", vol. 3, 1973, pp. 388-397 (With Certified English Translation).
K. Schrader: "Foundations and Formulations of Cosmetics",2-ND Edition, 1989, pp. 782-815 (With Certified English Translation).

* cited by examiner

*Primary Examiner*—Johann R Richter
*Assistant Examiner*—James H Alstrum Acevedo
(74) *Attorney, Agent, or Firm*—Michael J. Striker

(57) ABSTRACT

The foam product for hair treatment includes a composition containing a cationic cellulose derivative, chitosan, acid for partial or complete neutralization of the chitosan and a suitable solvent. The weight ratio of the cationic cellulose derivative to the chitosan is less than 2. The composition is either provided with a propellant or is foamed with a mechanically operated foam-making device.

10 Claims, No Drawings

AEROSOL FOAM OR PUMP FOAM PRODUCT FOR HAIR TREATMENT

CROSS-REFERENCE TO RELATED APPLICATIONS

This application claims priority under 35 U.S.C. 119(a)-(d) to German Patent Application DE 10221449.2, filed 5 May 2002.

BACKGROUND OF THE INVENTION

1. Field of the Invention

The subject matter of the invention is an aerosol foam or a pump foam product for hair treatment including a composition containing a cationic cellulose derivative, chitosan, an acid for partially or complete neutralization of chitosan and if necessary a propellant in a suitable solvent, in which the cationic cellulose derivative and the chitosan are present in a certain amount ratio.

2. Description of the Related Art

Foams for hair treatment are known and usually include hair-fixing or hair-care substances, foam-formers and a suitable aqueous solvent base. These compositions are foamed prior to application by means of a propellant gas or by means of a mechanically operated pump foam apparatus. These different types of foam products have different requirements regarding their quality, which can be roughly divided into two categories or groups. The first group of quality requirements deals with foam quality, i.e. the properties of the foam. These foam properties include fine porosity or coarse porosity, compactness, stability of the foam over time, workability into the hair and distributability of it on the hair. The second group of quality requirements relate to the action, which is produced by the foam after working it into the hair, i.e. the hair-care properties, such as the feel of the hair under moist and dry conditions, the combability, the fixing action, the load on the hair, the luster of the hair, etc.

The problem with the optimization of the foam products is that improvements of some quality requirements, for example the foam quality, can be achieved by addition of special active ingredients. However this usually results in the impairment of other quality requirements, for example the hair care or hair fixing properties. Frequently cationic polymers are contained in foam products because of their good substantive activity on human hair. Foam concentrates are known containing a certain amount of Polyquaternium-4 and chitosan lactate from WO 99/66888 A1. However addition of cationic cellulose derivatives, such as a copolymer of hydroxyethyl cellulose and diallyldimethyl ammonium chloride (Polyquaternium-4), has the disadvantage that the treated hair feels greasy and has a comparatively great load. A residue problem is frequently caused by use of neutralized chitosan (chitizonium salt); i.e. small amounts of a visible polymeric residue can be observed on the treated hair after treatment.

SUMMARY OF THE INVENTION

Thus it is an object of the present invention to optimize the quality requirements of foam products for hair treatment in regard to foam quality and hair care or hair fixing properties and to avoid the above-described disadvantages.

It has now been found that this object is attained in an outstanding manner by the subsequently described foam product.

The term "aerosol foam product" understandably means a product, which comprises a liquid foamable composition, which is filled into a pressurized container together with a propellant gas, which is provided with a foam head. This foam is produced from liquid foamable composition immediately prior to application by using the foam head.

The term "pump foam product" is a product, which comprises a liquid, foamable composition, which is filled in a container without a propellant, which container is provided with a mechanically operated device for foam production (foam pump). The foam is produced from this liquid foamable composition immediately prior to application using the mechanically operated device.

The subject matter of the invention is an aerosol foam product or pump foam product for hair treatment, which includes a composition containing (A) at least one cationic cellulose derivative;
(B) at least one chitosan,
(C) at least one acid for neutralization of the chitosan, and
(D) a suitable solvent system;

wherein the weight ratio of the cationic cellulose derivative (A) to the chitosan (B) is less than 2, preferably from 1:2 to 1.5:1 and the composition is either filled into a pressure-resistant container together with at least one propellant (E) or into a container with a mechanical device for foam production without a propellant.

Cationic Cellulose Derivative (A)

The cationic cellulose derivative (A) is contained in the composition according to the invention, preferably in an amount of 0.1 to 10, especially preferably from 0.5 to 5 percent by weight. Suitable cellulose derivatives are those, which contain at least one quaternary ammonium group, e.g. a copolymer of hydroxyethyl cellulose and diallyldimethylammonium chloride (Polyquaternium-4) or the reaction product of hydroxyethyl cellulose and an epoxide substituted with a trialkylammonium group (Polyquaternium-10), which can have alkyl groups with 1 to 20 carbon atoms, preferably methyl groups. The molecular weight is preferably between 100,000 to 600,000, especially preferably between 200,000 and 400,000, g/mol. The nitrogen content amounts to preferably from 0.5 to 4 percent by weight, especially preferably 1.5 to 3 percent by weight. The preferred cellulose derivative is Polyquaternium-4, which is marketed under the trademark CELQUAT® H100 and CELQUAT® L200, of which CELQUAT® L200 is especially preferred.

Chitosan (B)

The chitosan (B) is contained in the composition according to the invention preferably in an amount of 0.1 to 10, especially preferably from 0.5 to 5 percent by weight. The chitosan according to the invention is a completely or partially deacylated chitin. The chitosan to be used in the invention is preferably made from chitin contained in the shell residues of Crustacians, which is an inexpensive and natural raw material available in large quantity. The molecular weights of the chitosan can vary over a broad range for example from 20,000 to about 5 million g/mol. Low molecular weight chitosan with molecular weights from 30,000 to 70,000 g/mol is, for example, suitable. Molecular weights above 100,000 g/mol are preferred however. Molecular weights of 200,000 to 700,000 g/mol are however particularly preferred. The deacetylation degree preferably is from 10 to 99%, especially preferably from 60 to 99%

A suitable chitosan is, for example, marketed under the trademark FLONAC®, by Kyowa Oil & Fat, Japan. It has a molecular weight between 300,000 and 700,000 g/mol and a deacetylation degree of 70 to 80%. A preferred chitosan salt is chitosonium pyrrolidone carboxylate, which is marketed for example under the trademark KYTAMER® PC of Amerchol, USA. The contained chitosan has a molecular weight between 200,000 to 300,00 g/mol and a deacetylation degree of 70 to 85%. The chitosans used in the invention can also include chitosan derivatives, especially alkylated or hydroxyalkylated derivative compounds, for example hydroxyethyl chitosan, hydroxypropyl chitosan or hydroxybutyl chitosan. In a particularly preferred embodiment two chitosans with different molecular weights are contained and indeed a first chitosan with a molecular weight between 300,000 and 700,000 g/mol and a second chitosan with a molecular weight between 10,000 and 150,000 g/mol.

Neutralization Agent (C)

The chitosan or chitosan derivatives are present in completely or partially neutralized form. The neutralization degree is preferably at least 50%, especially preferably from 70 to 100%, based on the number of free base groups. In principle all cosmetically compatible inorganic or organic acids are used, e.g. formic acid, tartaric acid, malic acid, lactic acid, citric acid, pyrrolidone carboxylic acid and hydrochloric acid. Among others, pyrrolidone carboxylic acid, formic acid and lactic acid are especially preferred.

Solvent System (D)

The composition according to the invention is embodied in a purely aqueous or in an aqueous-alcoholic medium with preferably at least 50 percent by weight water and at least 5 percent by weight alcohol. The composition according to the invention preferably contains from 50 to 98, especially preferably from 75 to 95, percent by weight of the solvent system. The alcohol particularly can be a lower alcohol with one to four carbon atoms that is usually used for cosmetic purposes, e.g. ethanol and isopropanol. Organic solvents or mixtures of solvents with boiling points under 400° C. can be used as co-solvents in an amount of 0.1 to 15, preferably 1 to 10, percent by weight. Branched or unbranched hydrocarbons, such as pentane, hexane and isopentane, and cyclic hydrocarbons, such as cyclohexane and cyclopentane, are suitable as co-solvents. Glycerol, ethylene glycol and propylene glycol are especially preferred as water-soluble solvents.

Propellant (E)

The propellant (E) is preferably contained in the aerosol foam according to the invention in an amount of 1 to 20, especially preferably from 2 to 10, percent by weight. For example, lower alkanes, such as n-butane, i-butane, propane, butane or their mixtures, dimethyl ether or fluorinated hydrocarbons, such as 1,1-difluoroethane or tetrafluoroethane or their mixtures, or pressurized gaseous propellants, e.g. $N_2$, $N_2O$ and $CO_2$ and their mixtures, are suitable as the propellant in the composition according to the invention. Hydrocarbons with three to four carbon atoms are especially preferred as the propellant.

Surfactant (F)

A preferred embodiment of the foam product according to the invention contains at least one surfactant (F). The surfactant (F) is preferably contained in an amount of 0.01 to 15, especially preferably from 0.05 to 10, percent by weight. Suitable surfactants have emulsifying, solvating, foam-forming, foam-strengthening or hair-care properties, are preferably cationic or nonionic and have an HLB value of at most 20, preferably from 5 to 18. Especially preferred embodiments according to the invention contain both a nonionic surfactant and a cationic surfactant.

Ethoxylated surfactants, In which the number of ethylene oxide units is between 1 to 1000, preferably from 1 to 300, especially preferably from 1 to 15, are preferred nonionic surfactants. Fatty acid glyceride ethoxylates, fatty alcohol ethoxylates, fatty amine ethoxylates, fatty acid alkanol amide ethoxylates and fatty acid ester ethoxylates with one to fifty ethylene oxide units respectively are preferred. Suitable fatty alcohol ethoxylates are, for example, ethoxylated lauryl, tetradecyl, cetyl, oleyl or stearyl alcohol, which can be used alone or in a mixture, as well as fatty alcohols of ethoxylated lanolin or ethoxylates of lanolin. Also ethoxylated fatty alcohols, which are marked under the trademark DEHYDOL® of Henkel or under the trademark BRIJ® of ICI Surfactants, are suitable for hair treatment compositions according to the Invention. Under the fatty add ester ethoxylates, above all, diglyceride ethoxylates, should be named, for example ethoxylated castor oil with 25 ethylene oxide units with the INCI name PEG-25hydrogenated castor oil (ARLATONE® G), ethoxytated castor oil with 35 ethylene oxide units with the INCI name PEG-35 castor oil (CREMOPHOR® E1) or ethoxylated hydrogenated castor oil ethoxylated with 40 ethylene oxide units with the INCI name PEG-40 hydrogenated castor oil (CREMOPHOR® RH 410). Additional suitable nonionic surfactants Include ethoxylated fatty acid sugar esters, especially ethoxylated sorbitan fatty add esters, which are known as polysorbates. but also non-ethoxylated surfactants, such as fatty acid sugar esters, which are marketed under the trademark TWEEN® and ARLACEL® by ICI Surfactants and alkylpolyglycosides, which are marked under the trademark PLANTAREN® or PLANTACARE® by Henkel or under the trademark ORAMIX®by Seppic.

Suitable cationic surfactants have a quaternary ammonium group and can be represented by the general formula (I):

$$N^{(+)} R^1 R^2 R^3 R^4 X^{(-)} \tag{I}$$

wherein $R^1$, $R^2$, $R^3$ and $R^4$, independently of each other, each represent an alkyl group, an aryl group, an alkoxy group, a polyoxyalkylene group, an alkylamido group, a hydroxyalkyl group, an aryl group or an alkyaryl group with 1 to 22carbon atoms and $X^{(-)}$ represents an anion, e.g. a halogen, an acetate, phosphate, nitrate or alkyl sulfate, preferably a chloride or bromide. The aliphatic groups can also contain cross-bonds or other groups, such as amino groups, in addition to carbon and hydrogen. For example, suitable cationic surfactants are the chlorides or bromides of alkyldimethylbenzyl ammonium salts or alkyl-trimethyl ammonium salts, e.g. cetyltrimethylammonium chloride or -bromide, tetradecyltrimethylammonium chloride or -bromide, alkyldimethylhydroxyethyl-ammonium chloride or -bromide, dialkyldimethylammonium chloride or -bromide, alkylpyridinium salts, e.g. lauryl- or cetyl-pyridinium chloride, alkylamidoethyl-trimethylammonium ether sulfate and compounds with a cationic character, such as amine oxides, e.g. alkyl-methylamine oxides or alkylaminoethyldimethylamine oxides. Cetyltrimethylammonium chloride is especially preferred.

The product according to the invention also contains at least one film-forming nonionic polymer in a further preferred embodiment. The nonionic polymer is preferably contained in an amount of 0.01 to 15 percent by weight, especially preferably from 0.5 to 10 percent by weight. It can be a synthetic, natural or a modified natural polymer. Especially those polymers, which have a sufficient solubility in water or water/alcohol mixtures, so that they can be present in a completely dissolved form in the compositions according to the invention, are preferred. The term "film-forming polymers" means those polymers, which when used in an 0.01 to 5 percent aqueous, alcoholic or aqueous-alcoholic solution or dispersion are in a position, to deposit a polymer film on the hair.

Suitable synthetic nonionic film-forming polymers include homopolymers or copolymers, which are built up from at least one of the following monomers: vinyl pyrrolidone, vinyl caprolactam, vinyl ester (e.g. vinyl acetate), vinyl alcohol, acrylamide, methacrylamide, alkylacrylamides, dialkylacrylamides, alkylmethacrylamides, dialkylmethacrylamides, alkylacrylates, alkylmethacrylates, propylene glycol or ethylene glycol, in which the alkyl groups of these monomers are preferably C1- to C7-alkyl groups, especially preferably C1- to C3-alkyl groups. For example, homopolymers of vinyl caprolactam, homopolymers of vinyl pyrrolidone or homopolymers of N-vinylformamide, copolymers of vinyl pyrrolidone and vinyl acetate, terpolymers of vinyl pyrrolidone, vinyl acetate and vinyl propionate, polyacrylamides, polyvinyl alcohols and polyethylene glycol/polypropylene glycol copolymers are preferred. Polyvinyl pyrrolidone and copolymers of vinyl pyrrolidone and nonionic comonomers, e.g. polyvinylpyrrolidone/vinyl acetate copolymers, are especially preferred. Suitable natural film-forming polymers include, e.g., hydroxyalkylated polysaccharides, especially hydroxyalkyl cellulose or hydroxyalkyl guar with preferably 2 or 3 carbon atoms in the alkyl groups.

Special embodiments of the products according to the invention are hair coloring or hair dyeing products, especially coloring fixing compositions. These compositions contain at least one hair coloring or dyeing substance. This can be a soluble organic dyestuff, especially a so-called direct dye compound or an inorganic or organic pigment.

The total amount of dyestuffs or dye precursor compounds in the composition of the invention is preferably about 0.01 to 7 percent by weight, especially preferably from about 0.2 to 4 percent by weight. Suitable direct-dyeing dye compounds include e.g. triphenylmethane dye compounds, aromatic nitro dye compounds, azo dye compounds, quinone dye compounds, cationic or anionic dye compounds. The following compounds are suitable:

Nitro Dye Compounds (Blue):
1,4-bis[(2-hydroxyethyl)amino]-2-nitrobenzene, 1-(2-Hydroxyethyl)amino-2-nitro-4-[di(2-hydroxyethyl)amino]-benzene (HC Blue No. 2), 1-Amino-3-methyl-4-[(2-hydroxyethyl)amino]-6-nitrobenzene (HC Violet No. 1), 4-[Ethyl-(2-hydroxyethyl)-amino]-1-[(2-hydroxyethyl)amino]-2-nitrobenzene hydrochloride (HC Blue No. 12), 4-[Di(2-hydroxyethyl)amino]-1-[(2-methoxyethyl)amino]-2-nitrobenzene (HC Blue No. 11), 1-[(2,3-Dihydroxypropyl)amino]-4-[methyl-(2-hydroxyethyl)amino]-2-nitrobenzene (HC Blue No. 10), 1-[(2,3-Dihydroxypropyl)-amino]-4-[ethyl-(2-hydroxyethyl)amino]-2-nitrobenzene hydrochloride (HC Blue No. 9), 1-(3-Hydroxypropylamino)-4-[di(2-hydroxyethyl)amino]-2-nitrobenzene (HC Violet No. 2), 1-Methylamino-4-[methyl-(2,3-dihydroxypropyl)amino]-2-nitrobenzene (HC Blue No. 6), 2-((4-Amino-2-nitrophenyl)amino)-5-dimethylaminobenzoic acid (HC Blue No. 13), 1-(2-Aminoethylamino)-4-[di(2-hydroxyethyl)amino]-2-nitrobenzene, 4-(Di(2-hydroxyethyl)amino)-2-nitro-1-phenylaminobenzene.

Nitro Dye Compounds (red):
1-Amino-4-[(2-hydroxyethyl)amino]-2-nitrobenzene (HC Red No. 7), 2-Amino-4, 6-dinitrophenol, 1,4-Diamino-2-nitrobenzene (Cl76070), 4-Amino-2-nitro-diphenylamine (HC Red No. 1), 1-Amino-4-[di(2-hydroxyethyi)amino]-2-nitro-benzene hydrochloride(HC Red No. 13), 1-Amino-5-chloro-4-[(2-hydroxyethyl)-amino]-2-nitrobenzene, 4-Amino-1-[(2-hydroxyethyl)amino]-2-nitrobenzene (HC Red No. 3), 4-((2-Hydroxyethyl)methylamino)-1-(methylamino)-2-nitro-benzene, 1-Amino-4-((2,3dihydroxypropyl)amino)-5-methyl-2-nitrobenzene, 1-Amino-4-(methylamino)-2-nitro-benzene, 4-Amino-4-nitro-1-((prop-2-en-1-yl) -amino)benzene, 4-Amino-3-nitrophenol, 4-[(2-Hydroxyethyl)-amino]-3-nitro-phenol, 4-[(2-Nitrophenyl)amino]phenol (HC Orange No. 1), 1-[(2-Aminoethyl) -amino]-4-(2-hydroxyethoxy)-2-nitrobenzene (HC Orange No. 2), 4-(2,3-Dihydroxypropoxy)-1-[(2-hydroxyethyl)amino]-2-nitrobenzene (HC Orange No. 3), 1-Amino-5-chloro-4-[(2,3-dihydroxypropyl)amino]-2-nitrobenzene (HC Red No. 10), 5-Chloro-1, 4[-di(2,3-dihydroxypropyl)amino]-2-nitrobenzene(HC Red No. 11), 2-[(2-Hydroxyethyl)-amino]-4,6-dinitrophenol, 4-Ethylamino-3-nitrobenzoic acid, 2-[(4-Amino-2-nitrophenyl)amino]benzoic acid, 2-Chloro-6-ethylamino-4-nitro-phenol, 2-Amino-6-chloro-4-nitrophenol, 4-[(3-Hydroxypropyl)amino]-3-nitrophenol, 2,5-Diamino-6-nitropyridine, 6-Amino-3-((2-hydroxyethyl)amino)-2-nitropyridine, 3-Amino-6-((2-hydraxyethyl)amino) -2-nitropyridine, 3-Amino-6-(ethylamino)-2-nitropyridine, 3-((2-Hydroxyethyl) -amino)-6-(methyl-amino)-2-nitropyridine, 3-Amino-6-(methylamino)-2-nitro-pyridine, 6-(Ethylamino)-3-((2-hydroxyethyl)amino)-2-nitropyridine, 1,2,3,4-Tetrahydro-6-nitroquinoxaline, 7-Amino-3,4-dihydro-6-nitro-2H-1,4-benzoxazine (HC Red No. 14).

Nitro Dye Compounds (yellow):
1,2-Diamino-4-nitrobenzene (Cl76020),1-Amino-2-[(2-hydroxyethyl)amino]-5-nitrobenzene (HC Yellow No. 5), 1-(2-Hydroxyethoxy)-2-[(2-hydroxyethyl) -amino]-5-nitrobenzene (HC Yellow No. 4), 1-[(2-Hydroxyethyl)amino]-2-nitrobenzene (HC Yellow No. 2), 2-(Di(2-hydroxyethyl)amino)-5-nitrophenol, 2-[(2-Hydroxyethyl)-amino]-1-methoxy-5-nitrobenzene, 2-Amino-3-nitrophenol, 1-Amino-2-methyl-6-nitrobenzene, 1-(2-Hydroxyethoxy)-3-methylamino-4-nitro-benzene, 2,3-(Dihydroxypropoxy)-3-methylamino-4-nitrobenzene, 2-[(2-Hydroxyethyl) amino]-5-nitrophenol (HC Yellow No. 11), 3-[(2-Aminoethyl)amino]-1-methoxy -4-nitrobenzene hydrochloride (HC Yellow No.9), 1-[(2-Ureidoethyl)-amino]-4-nitrobenzene, 4-[(2,3-Dihydroxypropyl)amino]-3-nitro-1-trifluormethyl-benzene (HC Yellow No. 6), 1-Chloro-2,4-bis[(2-hydroxyethyl)amino]-5-nitrobenzene (HC Yellow No. 10), 1-Amino-4-((2-aminoethyl)amino)-5-methyl-2-nitrobenzene, 4-[(2-Hydroxyethyl)-amino]-3-nitro-1-methylbenzene, 1-Chloro-4-[(2-hydroxyethyl)amino]3-nitrobenzene (HC Yellow No. 12), 4-[(2-hydroxyethyl)amino]-3-nitro-1-trifluoromethylbenzene (HC Yellow No. 13), 4[(2-Hydroxyethyl)amino]-3.-nitrobenzonitrile (HC Yellow No. 14), 4-[(2-Hydroxyethyl)amino]-3-nitrobenzamide (HC Yellow No. 15), 3-((2-Hydroxyethyl)amino)-4-methyl-1-nitrobenzene, 4-Chloro-3-((2-hydroxyethyl)-amino)-1-nitrobenzene.

Quinone Dye Compounds:
1,4-Di[(2,3-dihydroxypropyl)amino]-9,10-anthraquinone, 1,4-Di[(2-hydroxyethyl)amino]-9,10-anthraquinone (Cl61545 Disperse Blue 23), 1-[(2-Hydroxyethyl)amino]-4-methylamino-9,10-anthraquinone (Cl61505, Disperse Blue No. 3), 2-[(2-Aminoethyl)amino]-9,10-anthraquinone (HC Orange No. 5), 1-Amino-4-hydroxy-9,10-anthraquinone (Cl60710, Disperse Red 15), 1-Hydroxy-4-[(4-methyl-2-sulfophenyl)amino]-9,10-anthraquinone, 7-Beta-D-glucopyranosyl-9,10-dihydro-1-methyl-9,10-dioxo-3,5,6,8-tetrahydroxy-2-anthracene carboxylic acid (Cl75470, Natural Red 4), 1-[(3-Aminopropyl)amino]-4-methylamino-9,10-anthraquinone (HC Blue No. 8), 1-[(3-Aminopropyl)amino]-9,10-anthraquinone (HC Red No. 8), 1,4-Diamino-2-methoxy-9,10-anthraquinone (Cl62015, Disperse Red No. 11, Solvent Violet No. 26), 1,4-Dihydroxy-5,8-bis[(2-hydroxyethyl)

amino]-9,10-anthraquinone (CI62500, Disperse Blue No. 7, Solvent Blue No. 69), 1,4-Diamino-9,10-anthraquinone (CI61100, Disperse Violet No. 1), 1-Amino-4-(methylamino)-9,10-anthraquinone (CI61105, Disperse Violet No. 4, Solvent Violet No. 12), 2-Hydroxy-3-methoxy-1,4-naphthaquinone, 2,5-Dihydroxy-1,4-naphthaquinone, 2-Hydroxy-3-methyl-1,4-naphthaquinone, N-(6-((3-Chloro-4-(methylamino)phenyl)imino)-4-methyl-3-oxo-1,4-cyclohexadien-1-yl)urea (HC Red No. 9), 2-((4-(Di(2-hydroxyethyl)amino)phenyl)amino)-5-((2-hydroxyethyl) amino)-2,5-cyclohexadien-1,4-dione (HC Green No. 1), 5-Hydroxy-1,4-naphthaquinone (CI75500, Natural Brown No. 7), 2-Hydroxy-1,4-naphthoquinone (CI75480, Natural Orange No. 6), 1,2-Dihydro-2-(1,3-dihydro-3-oxo-2H-indol-2-yliden)-3H-indol-3-one (CI73000), 4-((5-((2-Hydroxyethyl)amino-1-methyl-1H-pyrazol-4-yl)imino)-4,5-dihydro-5-((2-hydroxyethyl)-imino)-1-methyl-1H-pyrazole sulfate (1:1), hydrate (1:1).

Basic Dye Compounds:
9-(Dimethylamino)-benzo[a]phenoxazin-7-ium chloride (CI51175; Basic Blue No.6), Di[4-(diethylamino)phenyl][4-(ethylamino)naphthyl]carbenium chloride (CI42595; Basic Blue No. 7), Di-(4-(dimethylamino)phenyl)-(4-(methylphenylamino)-napthalene-1-yl)carbenium chloride (CI42563; Basic Blue No. 8), 3,7-Di(dimethylamino)phenothiazin-5-ium chloride (CI52015 Basic Blue No. 9), Di[4-(dimethylamino)phenyl][4-(phenylamino)naphthyl] carbenium chloride (CI44045; Basic Blue No.26), 2-[(4-(Ethyl(2-hydroxyethyl)amino)phenyl)azo]-6-methoxy-3-methyl-benzothiazolium methyl sulfate (CI11154; Basic Blue No. 41), 8-Amino-2-bromo-5-hydroxy-4-imino-6-[(3-(trimethylammonio)-phenyl)amino]-1(4H)-napthalinone chloride (CI56059; Basic Blue No. 99), bis-[4-(dimethylamino)phenyl]-[4-(methylamino)phenyl]carbenium chloride (CI42535; Basic Violet No. 1), Tri(4-amino-3-methylphenyl)carbenium chloride (CI42520;Basic Violet No. 2), Tris[4-(dimethylamino)-phenyl]carbenium chloride (CI42555;Basic Violet No. 3), 2-[3,6-(Diethylamino) dibenzopyranium-9-yl]-benzoic acid chloride (C145170; Basic Violet No. 10), Di(4-aminophenyl)(4-amino-3-methylphenyl)carbenium chloride (CI42510 Basic Violet No. 14), 1,3-bis[(2,4-diamino-5-methylphenyl)azo]-3-methylbenzene (CI21010; Basic Brown No. 4), 1-[(4-Aminophenyl)azo]-7-(trimethylammonio)-2-naphthol chloride (CI12250;Basic Brown No. 16), 3-[(4-Amino-2,5-dimethoxyphenyl)azo]-N,N,N-trimethylbenzene aminium chloride (CI112605, Basic Orange No. 69), 1-[(4-Amino-2-nitrophenyl)azo]-7-(trimethylammonio)-2-naphthol chloride, 1-[(4-Amino-3-nitrophenyl)azo]-7-(trimethylammonio)-2-naphthol chloride (CI12251; Basic Brown No. 17), 3,7-Diamino-2,8-dimethyl-5-phenylphenazinium chloride (CI50240; Basic Red No. 2), 1,4-Dimethyl-5-[(4-(dimethylamino)phenyl)azo]-1,2,4-triazolium chloride (CI11055; Basic Red No. 22), 2-Hydroxy-1-[(2-methoxyphenyl)azo]-7-(trimethylammonio)-napthalene chloride (CI12245; Basic Red No. 76), 2-[2-((2,4-Dimethoxyphenyl)amino)ethenyl]-1,3,3-trimethyl-3H-indolium chloride (CI48055; Basic Yellow No. 11), 3-Methyl-1-phenyl-4-[(3-(trimethylammonio)phenyl) azo]-pyrazol-5-one chloride (CI12719; Basic Yellow No. 57), Di[4-(dimethylamino)phenyl]-iminomethane hydrochloride (CI41000; Basic Yellow No. 2), bis-[4-(diethylamino)-phenyl]phenyl carbenium hydrogen sulfate (1:1) (CI42040; Basic Green No. 1), Di(4-(dimethylamino)phenyl)phenylmethanol (CI42000; Basic Green No. 4), 1-(2-Morpholinium-propylamino)-4-hydroxy-9,10-anthraquinone methyl sulfate, 1-((3-(Dimethylpropylaminium)propyl)amino)-4-(methylamino)-9,10-anthraquinone chloride.

Neutral Azo Dye Compounds:
1-[Di(2-hydroxyethyl)amino]-3-methyl-4-[(4-nitrophenyl) azo]-benzene (CI11210,Disperse Red No. 17), 1-[Di(2-hydroxyethyl)amino]-4-[(4-nitrophenyl)azo]-benzene (Disperse Black No. 9), 4-[(4-Aminophenyl)azo]-1-[di(2-hydroxyethyl)amino]-3-methylbenzene (HC Yellow No. 7), 2,6-Diamino-3-[(pyridine-3-yl)azo]-pyridine, 2-((4-(Acetylamino)phenyl)azo)-4-methylphenol (CI11855; Disperse Yellow No. 3).

Acid Dye Compounds:
6-Hydroxy-5-[(4-sulfophenyl)azo]-2-napthalene sulfonic acid disodium salt (CI15985; Food Yellow No. 3; FD&C Yellow No. 6), 2,4-Dinitro-1-naphthol-7-sulfonic acid disodium salt (CI10316; Acid Yellow No. 1; Food Yellow No. 1), 2-(Indan-1,3-dion-2-yl)quinolin-x,x-sulfonic acid (mixture of mono and disulfonic acids) (CI47005; D&C Yellow No. 10; Food Yellow No. 13; Acid Yellow No. 3), 5-Hydroxy-1-(4-sulfophenyl)-4-[(4-sulfophenyl)azo] pyrazol-3-carboxylic acid trisodium salt (CI19140; Food Yellow No. 4; Acid Yellow No. 23), 9-(2-Carboxyphenyl)-6-hydroxy-3H-xanthen-3-one (CI45350; Acid-Yellow No. 73; D&C Yellow No. 8), 4-((4-Amino-3-sulfophenyl)azo) benzenesulfonic acid disodium salt (CI13015, Acid Yellow No. 9), 5-[(2,4-Dinitrophenyl)amino]-2-phenylaminobenzene sulfonic acid sodium salt (CI10385; Acid Orange No. 3), 4-[(2,4-Dihydroxyphenyl)azo]benzene sulfonic acid monosodium salt (CI14270; Acid Orange No. 6), 4-[(2-Hydroxynaphth-1-yl)azo]-benzene sulfonic acid sodium salt (CI15510; Acid Orange No. 7), 4-[(2,4-Dihydroxy-3-[(2,4-dimethylphenyl)azo]-phenyl)azo]-benzene sulfonic acid sodium salt (CI20170; Acid Orange No. 24), 4-Hydroxy-3-[(4-sulfonaphth-1-yl)azo]-1-napthalene sulfonic acid disodium salt (CI14720; Acid Red No. 14), 4-Hydroxy-3-[(2-methoxyphenyl)azo]-1-naphtalene sulfonic acid monosodium salt (CI14710; Acid Red No. 4), 6-Hydroxy-5-[(4-sulfonaphth-1-yl)azol-2,4-napthalene-disulfonic acid trisodium salt (CI16255; Ponceau 4R; Acid Red No. 18), 3-Hydroxy-4-[(4-sulfonaphth-1-yl)azo]-2,7-napthalene-disulfonic acid trisodium salt (CI16185; Acid Red No. 27), 8-Amino-1-hydroxy-2-(phenyl-azo)-3,6-napthalene-disulfonic acid disodium salt (CI17200; Acid Red No. 33), 5-(acetylamino)-4-hydroxy-3-[(2-methylphenyl)azo]-2,7-napthalene disulfonic acid disodium salt (CI18065; Acid Red No. 35), 2-(3-Hydroxy-2,4,5,7-tetraiodo-dibenzopyran-6-on-9-yl)-benzoic acid disodium salt (CI45430; Acid Red No. 51), N-[6-(Diethylamino)-9-(2,4-disulfophenyl)-3H-xanthen-3-yliden]-N-ethyl ethane ammonium hydroxide, inner salt, sodium salt (CI45100; Acid Red No. 52), 8-[(4-(Phenylazo)phenyl)azo]-7-naphthol-1,3-disulfonic acid disodium salt (CI27290; Acid Red No. 73), 2',4',5',7'-Tetrabrom-3',6'-dihydroxyspiro[isobenzofuran-1(3H),9'-[9H]xanthen]-3-one disodium salt (CI45380 Acid Red No. 87), 2',4',5',7'-Tetrabromo-4,5,6,7-tetrachloro-3',6'-dihydroxyspiro-[isobenzofuran-1(3H), 9'[9H]xanthen]-3-one disodium salt (CI45410; Acid Red No. 92), 3',6'-Dihydroxy-4',5'-diiodospiro[isobenzofuran-1(3H),91(9H)-xanthen]-3-one sodium salt (CI45425; Acid Red No. 95), 2-Hydroxy-3-((2-hydroxynaphth-1-yl) azo)-5-nitrobenzene sulfonic acid monosodium salt (CI15685; Acid Red No. 184), (2-Sulfophenyl)-di[4-(ethyl ((4-sulfophenyl)methyl)amino)phenyl]-carbenium, disodium salt, betaine (CI42090; Acid Blue No. 9; FD&C Blue No. 1), 1,4-bis-[(2-sulfo-4-methylphenyl)amino]-9,10-anthraquinone-disodium salt (CI61570; Acid Green No. 25), bis[4-(dimethylamino)phenyl]-(3,7-disulfo-2-hydroxynaphth-1-yl)carbenium inner salt, monosodium salt (CI44090; Food Green No. 4; Acid Green No. 50), bis-[4-(diethylamino)-phenyl](2,4-disulfophenyl)carbenium inner salt, sodium salt (2:1) (CI42045; Food Blue No. 3;

Acid Blue No. 1), bis[4-(diethylamino)phenyl](5-hydroxy-2,4-disulfophenyl)-carbenium inner salt, calcium salt (2:1) (Cl42051; Acid Blue No. 3), 1-Amino-4-(cyclohexylamino)-9,10-anthraquinone-2-sulfonic acid sodium salt (Cl62045; Acid Blue No. 62), 1-Amino-4-(phenylamino)-9,10-anthraquinone-2-sulfonic acid (Cl62055; Acid Blue No. 25), 2-(1,3-Dihydro-3-oxo-5-sulfo-2H-indol-2-yliden)-2,3-dihydro-3-oxo-1H-indol-5-sulfonic acid disodium salt (Cl73015; Acid Blue No. 74), 9-(2-carboxyphenyl)-3-[(2-methylphenyl)amino]-6-[(2-methyl-4-sulfophenyl)amino]xanthylium inner salt, monosodium salt (Cl45190; Acid Violet No. 9), 1-Hydroxy-4-[(4-methyl-2-sulfophenyl)amino]-9,10-anthraquinone-sodium salt (Cl60730; D&C Violet No. 2; Acid Violet No. 43), bis[3-nitro-4-[(4-phenylamino)-3-sulfophenylamino]-phenyl]sulfone (Cl10410; Acid Brown No. 13), 5-Amino-4-hydroxy-6-[(4-nitrophenyl)-azo]-3-(phenylazo)-2,7-napthalene disulfonic acid disodium salt (Cl20470; Acid Black No. 1), 3-Hydroxy-4-[(2-hydroxynaphth-1-yl)azo]-7-nitro-1-napthalene-sulfonic acid chromium complex (3:2) (Cl15711; Acid Black No. 52), 3-[(2,4-Dimethyl-5-sulfophenyl)azo]-4-hydroxy-1-napthalene sulfonic acid disodium salt (Cl14700; Food Red No. 1; Ponceau SX; FD&C Red No. 4), 4-(Acetylamino)-5-hydroxy-6-[(7-sulfo-4-[(4-sulfophenyl)azo] naphth-1-yl)azo]-1,7-napthalene disulfonic acid tetrasodium salt (Cl28440; Food Black No. 1), 3-Hydroxy-4-(3-methyl-5-oxo-1-phenyl-4,5-dihydro-1H-pyrazol-4-yl-azo)napthalene-1-sulfonic acid sodium salt, chromium complex (Acid Red No. 195).

E. Sagarin, "Cosmetics, Science and Technology", Interscience Publishers Inc., New York (1957), pp. 503 ff.; H. Janistyn, "Handbook of Cosmetics and Fragrances", Vol 3 (1973), pp. 388 ff. and K. Schrader "Foundations and Formulations of Cosmetics", $2^{nd}$ Ed. (1989), pp. 782 to 815 describe additional or further known and conventional hair dye compounds for dyeing hair, which can be contained in the hair dye compositions according to the invention.

Suitable hair dying pigments are coloring agents, which are practically insoluble in the application medium, and can be inorganic or organic. Also inorganic-organic mixed pigments are possible. The pigments however are preferably not nanopigments. The preferred particle size amounts to 1 to 200 μm, especially 3 to 150 μm, and even more preferably from 10 to 100 μm. Inorganic pigments are preferred. The inorganic pigments can be of a natural origin, for example chalk, ocher, umber, green earth, burnt Terra di Siena or graphite. The pigments can be white pigments, such as titanium dioxide or zinc oxide, black pigments, such as iron oxide black, colored pigments, such as ultramarine or iron oxide red, lustrous pigments, metal effect pigments, pearlescent pigments and fluorescence or phosphorescence pigments. Preferably at least one pigment is a non-white pigment. Metal oxides, metal hydroxides and metal oxihydrates, mixed phase pigments, sulfur-containing silicates, metal sulfides, complex metal cyanides, metal sulfates, metal chromates and metal molybdates, as well as metals themselves (Bronze pigments) are suitable. Especially titanium dioxide (Cl 77891), black iron oxide (Cl 77499), yellow iron oxide (Cl 77492), red and brown iron oxide (Cl 77491), manganese violet (Cl 77742), Ultramarine (Sodium aluminum sulfo silicate, Cl 77007, Pigment Blue 29), Chromium oxide hydrate (Cl 77289), iron blue (Ferric ferrocyanide, Cl 77510), Carmine (Cochineal), are suitable as the pigments in embodiments of the cosmetic preparations according to the invention. Pigments based on mica, which are coated with a metal oxide or a metal oxychloride, such as titanium dioxide or bismuth oxychloride and, if necessary, other coloring agents, such as iron oxides, iron blue, Ultramarine, Carmine, etc, are particularly preferred. The colors of these particular preferred pigments are determined by variation of the coating thickness. These pigments are marketed by Merck, Germany, under the trademarks RONA®, COLORONA®, DICHRONA® and TIMIRON®. Organic pigments include, e.g., the natural pigments sepia, gamboge, animal charcoal, Kasseler brown, indigo, chlorophyll and other plant pigments. Synthetic organic pigments are, e.g., azo pigments, anthraquinoid, indigoid, dioxazine, quinacridone, phthalocyanine, isoindolinone, perylene and perinone, metal complex, alkali blue and diketopyrrolopyrrole pigments.

The product according to the invention can also contain conventional cosmetic additives usually used in hair treatment compositions, e.g. perfume oils in an amount of 0.01 to 0.5 percent by weight; preservatives, such as parabene, in an amount of 0.01 to 1.0 percent by weight; buffer substances, such as sodium citrate or sodium phosphate, in an amount of 0.1 to 1.0 percent by weight; care substances, such as e.g. plant extracts and vegetable extracts, protein hydroylzates and silk hydrolyzates, lanolin derivatives, in an amount of 0.1 to 5 percent by weight; physiologically compatible silicone derivatives, such as volatile or non-volatile silicone oils or high molecular weight siloxane polymers in an amount of 0.05 to 20 percent by weight; light protective agents, antioxidants, radical-trapping agents, anti-flaking active ingredients, direct dye compounds, luster-imparting substances and combability-improving substances in an amount of 0.01 to 2 percent by weight.

The aerosol foam product according to the invention is filled in a pressure-resistant aerosol container or package, which is provided with a device for foaming production (aerosol foam head). When a foam is produced with this aerosol container or can, it is worked gently into the hair and rapidly breaks up when it is worked into the hair.

The method of using the cosmetic composition according to the invention comprises applying the composition to moist hand-towel dried hair in an amount sufficient to produce the desired hair-care or hair-fixing effect on the hair and is left on the hair without rinsing. Subsequently a hairstyle can be formed in the usual way or the hair can be set or curled and styled finally dry. However it is also possible to use the composition directly on dried hair.

Foam with good compact foam properties or quality is obtained, which breaks up quickly in the hair and is worked well into the hair. It is characterized by good styling properties, pleasant smooth feel of the moist and dry hair, good elasticity, no loading of the hair, beautiful luster and strong fixing.

The following examples illustrate the above-described invention in more detail, but the details in these examples should not be considered as limiting the claims appended hereinbelow.

EXAMPLES

Example 1A

Aerosol Hair Foam Composition of the Invention

| | | |
|---|---|---|
| 1 | g | Chitosan |
| 1 | g | CELQUAT ® L200 (Copolymer of hydroxyethyl cellulose and diallyldimethyl ammonium chloride; Polyquaternium-4) |
| 0.3 | g | Formic acid (85%) |
| 0.2 | g | Laureth-4 |
| 0.2 | g | Perfume |
| 0.15 | g | Cetyltrimethylammonium chloride |
| 10 | g | Ethanol |
| to 100 | g | Water |

Example 1B

Comparative Formulation

| | | |
|---|---|---|
| 0.67 | g | Chitosan |
| 1.33 | g | CELQUAT ® L200 (Copolymer of hydroxyethyl cellulose and diallyldimethyl ammonium chloride; Polyquaternium-4) |
| 0.22 | g | Formic acid (85%) |
| 0.2 | g | Laureth-4 |
| 0.2 | g | Perfume |
| 0.15 | g | Cetyltrimethylammonium chloride |
| 10 | g | Ethanol |
| to 100 | g | Water |

The effective ingredient mixtures were filled into respective aerosol cans together with 4.8 bar of propane/butane as propellant in a ratio 92:8. In salon trials test individuals were treated with respective equal amounts of the above two foams. The treated hair was judged by skilled professionals with their senses. Their decisions were as follows:

Foam 1A (the Invention):

The foam has a beautiful compact foam quality and may be easily distributed on the hair. The following styling properties are very good. The hair feels very good after drying, has a smooth feel, good elasticity, no load, a beautiful luster and a strong fixing.

Foam 1B (Comparative):

The foam has good foam quality and may be distributed on the hair. After application, the foam very greatly foams on the hair. The hair feels unpleasant, very greasy and soapy. The styling properties are not positive. The slidability is very heavy or impaired. After drying the hair is dull and does not have the special positive properties that the foam 1A has except for the strong fixing.

Example 2

Pump Foam

| | | |
|---|---|---|
| 0.5 | g | Chitosan |
| 0.5 | g | CELQUAT ® L200 (Copolymer of hydroxyethyl cellulose and diallyldimethyl ammonium chloride; Polyquaternium-4) |
| 1 | g | ABILQUAT ® 3272(Quaternium-80, 50% in Propylene glycol) |
| 0.5 | g | Cetyltrimethylammonium chloride |
| 0.15 | g | Formic acid (85%) |
| 5 | g | Ethanol |
| to 100 | g | Water |

Example 3

Aerosol Foam-fixing Composition

| | | |
|---|---|---|
| 1 | g | Chitosan |
| 1 | g | CELQUAT ® L200 (Copolymer of hydroxyethyl cellulose and diallyldimethyl ammonium chloride; Polyquaternium-4) |
| 0.85 | | Pyrrolidone carboxylic acid |
| 1.5 | g | Vinylpyrrolidone/vinyl acetate Copolymer (LUVISKOL ® VA64) |
| 0.2 | g | Laureth-4 |
| 0.3 | g | Perfume |
| 0.2 | g | Cetyltrimethylammonium chloride |
| to 100 | g | Water |

The effective ingredient mixture is filled into an aerosol can with a foam valve in a ratio 92:8 with propane/butane, 4.8 bar, as propellant.

Example 4

Aerosol Foam Composition

| | | |
|---|---|---|
| 1.25 | g | Chitosan (MW 20,000-100,000) |
| 0.3 | g | Chitosan (MW 300,000-700,000) |
| 1.25 | g | CELQUAT ® L200 (Copolymer of hydroxyethyl cellulose and diallyldimethyl ammonium chloride; Polyquaternium-4) |
| 0.4 | g | Formic acid (85%) |
| 0.25 | g | Perfume |
| 0.2 | g | Cetyltrimethylammonium chloride |
| 10 | g | Ethanol |
| to 100 | g | Water |

The effective ingredient mixture is filled into an aerosol can with a foam valve in a ratio 92:8 with propane/butane, 4.8 bar, as propellant.

Example 5

Foam-fixing and Dyeing Composition

| | | |
|---|---|---|
| 1 | g | Chitosan |
| 1 | g | CELQUAT ® L200 (Copolymer of hydroxyethyl cellulose and diallyldimethyl ammonium chloride; Polyquaternium-4) |
| 0.3 | g | Formic acid (85%) |
| 0.2 | g | Laureth-4 |
| 0.2 | g | Perfume |
| 0.11 | g | 3-[(2'-nitro-4'-(trifluoromethyl)phenyl)amino]-1,2-propandiol |
| 0.15 | g | Cetyltrimethylammonium chloride |
| 10 | g | Ethanol |
| to 100 | g | Water |

The effective ingredient mixture is filled into an aerosol can with a foam valve in a ratio 94:6 with propane/butane, 5 bar, as propellant.

Example 6

Coloring Mousse Red

| | | |
|---|---|---|
| 5.00 | g | TIMIRON ® STARLIGHT RED (Merck)* |
| 1 | g | Chitosan |
| 1 | g | CELQUAT ® L200 (Copolymer of hydroxyethyl cellulose and diallyldimethyl ammonium chloride; Polyquaternium-4) |
| 0.3 | g | Formic acid (85%) |
| 0.2 | g | Laureth-4 |
| 0.2 | g | Perfume |
| 0.15 | g | Cetyltrimethylammonium chloride |
| 10 | g | Ethanol |
| to 100 | g | Water |

*Mica/titanium dioxide pigment with red reflection color

The effective ingredient mixture is filled into an aerosol can with a foam valve in a ratio 94:6 with propane/butane, 5 bar, as propellant.

The disclosure in German Patent Application 102 21 449.2 of May 15, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in an aerosol foam or pump foam product for hair treatment, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. An aerosol or pump foam product for treating hair, said product comprising a container and a foamable composition contained in the container, wherein said foamable composition consists of:
   from 0.5 to 5 percent by weight of a copolymer of hydroxyethylcellulose and diallyldimethylammonium chloride with a molecular weight between 100,000 and 600,000 g/mol;
   from 0.5 to 5 percent by weight of at least one partially neutralized chitosan with a molecular weight from 20,000 to 5,000,000 g/mol, a neutralization degree of at least 50%, and a deacetylation degree of from 10 to 100%;
   at least one organic acid for partially neutralizing said at least one chitosan in an amount necessary for partially neutralizing said at least one chitosan, said at least one organic acid being selected from the group consisting of pyrrolidone carboxylic acid, formic acid, and lactic acid;
   from 50 to 98 percent by weight of a solvent system, said solvent system consisting of water or consisting of an aqueous-alcoholic medium containing at least 50 percent by weight water and at least 5 percent by weight of ethanol and/or isopropanol;
   from 0.05 to 10 percent by weight of at least one surfactant, wherein said at least one surfactant comprises a fatty alcohol ethoxylate and a cationic surfactant selected from the group consisting of alkyldimethylammonium chlorides, alkyldimethylammonium bromides, alkyltrimethylammonium chlorides, and alkyltrimethylammonium bromides, wherein the alkyl groups have from 1 to 22 carbon atoms; and
   at least one cosmetic ingredient selected from the group consisting of a direct dye compound, a perfume oil, a preservative, and a buffer substance;
   wherein said perfume oil is contained in the foamable composition in an amount of from 0.01 to 0.5 percent by weight when present in the composition, said buffer substance is contained in the foamable composition in an amount of from 0.1 to 1.0 percent by weight when present in the composition, said preservative is contained in the foamable composition in an amount of from 0.01 to 1.0 percent by weight when present in the composition, and said direct dye compound is contained in the foamable composition in an amount of from 0.01 to 4.0 percent by weight when present in the composition;
   wherein the copolymer and said at least one chitosan are present in the foamable composition in a weight ratio of from 1:2 to 1.5:1, and
   wherein the container is either a pressure-resistant container containing at least one propellant in addition to said foamable composition or is a pump foam container provided with a mechanical device for foam production without a propellant.

2. The foam product as defined in claim 1, wherein said at least one copolymer of hydroxyethylcellulose and diallyldimethylammonium chloride has a molecular weight between 200,000 and 400,000 g/mol and a nitrogen content of 1.5 to 3 percent by weight.

3. The foam product as defined in claim 1, wherein said at least one partially neutralized chitosan has a molecular weight over 100,000 g/mol and a deacetylation degree of at least 60%.

4. The foam product as defined in claim 1, wherein said at least one partially neutralized chitosan consists of two partially neutralized chitosans of different molecular weights.

5. The foam product as defined in claim 1, wherein said product contains said at least one propellant and said at least one propellant is propane, i-butane, n-butane or dimethyl ether or a mixture thereof.

6. The foam product as defined in claim 1, containing from 1 to 20 percent by weight of said at least one propellant.

7. The foam product as defined in claim 1, wherein at least one cosmetic ingredient is said direct dye compound.

8. The foam product as defined in claim 1, wherein the copolymer of hydroxyethylcellulose and diallyldimethylammonium chloride is polyquaternium-4.

9. A foam product for treating hair, said product comprising a composition for foam production and said composition consisting of:
   from 0.5 to 5 percent by weight of a copolymer of hydroxyethylcellulose and diallyldimethylammonium chloride with a molecular weight between 100,000 and 600,000 g/mol;
   from 0.5 to 5 percent by weight of a chitosan of a molecular weight of 200,000 to 700,000 g/mol and a deacetylation degree of at least 60%;
   at least one organic acid in an amount sufficient for neutralizing from 50 to 100 percent of said chitosan, said at least one organic acid being selected from the group consisting of pyrrolidone carboxylic acid, formic acid, and lactic acid;
   from 50 to 98 percent by weight of a solvent, said solvent consisting of water, ethanol, or isopropanol, or mixtures thereof;
   from 1 to 20 percent by weight of a $C_3$- to $C_4$-hydrocarbon as a propellant; wherein the copolymer and the chitosan are present in the composition in a weight ratio of from 1:2 to 1.5:1;
   from 0.05 to 10 percent by weight of at least one surfactant, wherein said at least one surfactant comprises a fatty alcohol ethoxylate and a cationic surfactant selected from the group consisting of alkyldimethylammonium chlorides, alkyldimethylammonium bromides, alkyltrimethylammonium chlorides, and alkyltrimethylammonium bromides, wherein the alky; groups have from 1 to 22 carbon atoms; and
   at least one cosmetic ingredient selected from the group consisting of a direct dye compound. a perfume oil, a preservative, and a buffer substance;
   wherein said perfume oil is contained in the composition in an amount of from 0.01 to 0.5 percent by weight when present in the composition, said buffer substance is contained in the composition in an amount of from 0.1 to 1.0 percent by weight when present in the composition, said preservative is contained in the composition in an amount of from 0.01 to 1.0 percent by weight when present in the composition, and said direct dye compound is contained in the composition in an amount of from 0.01 to 4.0 percent by weight when present in the composition.

10. The foam product as defined in claim 9 wherein the the copolymer of hydroxyathylcellulose and diallyldimethylammonium chloride is polyquaternium-4.

* * * * *

UNITED STATES PATENT AND TRADEMARK OFFICE
CERTIFICATE OF CORRECTION

PATENT NO. : 7,597,898 B2  Page 1 of 1
APPLICATION NO. : 10/435953
DATED : October 6, 2009
INVENTOR(S) : Birkel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 364 days.

Signed and Sealed this

Twenty-eighth Day of September, 2010

David J. Kappos
*Director of the United States Patent and Trademark Office*